United States Patent
Itaya et al.

(10) Patent No.: US 8,026,081 B2
(45) Date of Patent: Sep. 27, 2011

(54) METHOD OF PRODUCING OPTICALLY ACTIVE (S)-7-HYDROXY-6-METHYLHEPTAN-2-ONE AND PRECURSOR THEREOF

(75) Inventors: Nobushige Itaya, Nishinomiya (JP); Hiroshi Maeda, Osaka (JP); Yuki Sato, Amagasaki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 447 days.

(21) Appl. No.: 12/294,051

(22) PCT Filed: Mar. 22, 2007

(86) PCT No.: PCT/JP2007/056742
§ 371 (c)(1),
(2), (4) Date: Sep. 23, 2008

(87) PCT Pub. No.: WO2007/114199
PCT Pub. Date: Oct. 11, 2007

(65) Prior Publication Data
US 2009/0118534 A1    May 7, 2009

(30) Foreign Application Priority Data

Mar. 28, 2006 (JP) ................. 2006-089256
Sep. 22, 2006 (JP) ................. 2006-257384

(51) Int. Cl.
*C12P 1/00* (2006.01)
*C12P 7/62* (2006.01)
(52) U.S. Cl. ..................... 435/41; 435/135
(58) Field of Classification Search ........... 435/41, 435/135
See application file for complete search history.

(56) References Cited

U.S. PATENT DOCUMENTS

| 2003/0144523 A1 | 7/2003 | Klar et al. |
| 2009/0018342 A1 | 1/2009 | Klar et al. |

FOREIGN PATENT DOCUMENTS

| CA | 2531078 A1 | 1/2005 |
| DE | 19751200 A1 | 5/1999 |
| JP | 56127780 A | 10/1981 |
| JP | 57181039 A | 11/1982 |
| JP | 61033140 A | 2/1986 |
| JP | 10033191 A | 2/1998 |
| JP | 2007191400 A | 8/2007 |
| WO | 9907692 A2 | 2/1999 |
| WO | 2005003071 A1 | 1/2005 |
| WO | 2005101950 A1 | 11/2005 |

OTHER PUBLICATIONS

Schinzer, D., et al.: Studies Towards the Total Synthesis of Epothilones: Asymmetric Synthesis of the Key Fragments, Chem. Eur. J., 1996, 2, 11, pp. 1477-1482.
Ishibashi, M., et al.: The Stereochemistry of Variabilin, An Antimicrobial Sesterterpene Isolated from Marine Sponges, Natural Product Letters, 1993, 3, pp. 189-192.
Nicolaou, K.C., et al.: Total Syntheses of Epothilones A and B via a Macrolactonization-Based Strategy, J. Am. Chem. Soc., 1997, 119, pp. 7974-7991.
Issa, Hamad H., et al.: New Cytotoxic Furanosesterterpenes from an Okinawan Marine Sponge, *Ircinia* sp., J. Nat. Prod., 2003, 66, pp. 251-254.
Giersch, Wolfgang, et al.: 75. Enantiomeric 3,7-Dimethylocta-1,7-dienes as Useful Chiral Building Blocks, A New Access to Both Optical Antipodes of Natural (E)-3,7-Dimethyloct-2-ene-1,8-diol and (E)-3,7-Dimethyloct-2-ene-1,8- dicarboxylic Acid, Helvetica Chimica Acta, 1990, 73, pp. 733-738.
Wani, Mansukh C., et al.: Synthesis and Biological Activity of Zoapatanol Analogues, J. Med. Chem., 1983, 26, pp. 426-430.
Blaha, L., et al.: Claisen-Cyclisierung Einiger Ketoester Mit Alkalischen Hydroxiden, Collection Czechoslov. Chem. Commun., 1965, 30, pp. 1214-1220.
Singh, Rekha, et al.: Synthesis of enantiomerically pure all cis-2,3,6-trisubstituted piperidine: a silicon mediated total synthesis of (+)-carpamic acid, Tetrahedron Letters, 2002, 43, pp. 7711-7715.
Dhokte, U.P., et al.: Synthesis of the Pheromones, (E)-3,7-Dimethyl-2,7-Octadienyl Propionate, (E)-3,7-Dimethyl-2- Octene-1,8-Diol and Frontalin from a Common Intermediate, Synthetic Communications, 1988, 18(8), pp. 811-822.
Odinokov, V.N., et al.: Ozonolysis of alkenes and the reactions of polyfunctional compounds. LIV. Selective ozonolysis of (s)-(+)-dihydromyrcene and the synthesis of pheromones of the Chinese bean weevil (*Callosobruchus chinensis*) and the African monarch (*Dansus chysippus*), Zhurnal Organicheskoi Khimii, 1993, 29, 1, pp. 39-43.

*Primary Examiner* — Tekchand Saidha
(74) *Attorney, Agent, or Firm* — Panitch Schwarze Belisario & Nadel LLP

(57) ABSTRACT

Provided is a method capable of industrially producing optically active (S)-7-hydroxy-6-methylheptan-2-one and its precursor simply and efficiently. The production method, allows a R-body preferentially hydrolyzable *Aspergillus* microorganism-derived esterase to act on a 2-methyl-6-oxoheptanoate (II), to produce an optically active (S)-2-methyl-6-oxoheptanoate (III).

13 Claims, No Drawings

US 8,026,081 B2

METHOD OF PRODUCING OPTICALLY ACTIVE (S)-7-HYDROXY-6-METHYLHEPTAN-2-ONE AND PRECURSOR THEREOF

CROSS-REFERENCE TO RELATED APPLICATION

This application is a section 371 of International Application No. PCT/JP2007/056742, Filed Mar. 22, 2007, which was published in the Japanese language on Oct. 11, 2007 under International Publication No. WO 2007/114199 A1 and the disclosure of which is incorporated herein by reference.

TECHNICAL FIELD

The present invention relates to a method of producing optically active (S)-7-hydroxy-6-methylheptan-2-one and a precursor thereof.

BACKGROUND ART

Epothilone derivatives of the following formula are useful as an anti-cancer agent.

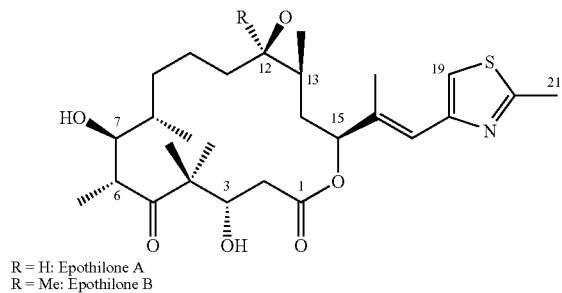

R = H: Epothilone A
R = Me: Epothilone B

In synthesis of Epothilone derivatives, optically active (S)-7-hydroxy-6-methylheptan-2-one is useful as a $C_7$ to $C_{12}$ building block, and this compound can be derived from optically active (S)-2-methyl-6-oxoheptanoic acid via its ester (see, patent documents 1 and 2, non-patent documents 1 and 2). For 2-methyl-6-oxoheptanoic acid, various production methods are suggested (see, non-patent documents 3 to 8). In the production methods described in non-patent documents 3 to 6, however, raw material availability is problematic since corresponding natural materials are extracted and isolated, and oxidized in these methods. The production method described in non-patent document 6 is a method of producing a (R) body. The production methods described in non-patent documents 7 and 8 are methods for oxidizing 2,6-dimethyl-cyclohexanone using potassium permanganate, however, the resultant product is a racemate of 2-methyl-6-oxoheptanoic acid, and is optically inactive.

[patent document 1] DE 19751200
[patent document 2] WO 2005/003071
[non-patent document 1] J.A.C.S., 119, 7974 (1997)
[non-patent document 2] Chem. Eur. J., 2, 1477 (1996)
[non-patent document 3] Natural Product Letters, 3, 189 (1993)
[non-patent document 4] J. Nat. Prod., 66, 251 (2003)
[non-patent document 5] Natural Product Letters, 4, 51 (1994)
[non-patent document 6] Helv. Chim. Acta, 73, 733 (1990)
[non-patent document 7] J. Med. Chem., 26, 426 (1983)
[non-patent document 8] Collect. Czech. Chem. Commun., 30, 1214 (1965)

DISCLOSURE OF THE INVENTION

An object of the present invention is to provide a method capable of industrially producing optically active (S)-7-hydroxy-6-methylheptan-2-one and its precursor optically active (S)-2-methyl-6-oxoheptanoate or the like, simply and efficiently.

The present inventors have obtained a knowledge that when a 2-methyl-6-oxoheptanoate (RS mixture) is optically resolved by acting a specific esterase, an (S) body is obtained with high optical purity, and found that if this optical resolution is utilized, optically active (S)-7-hydroxy-6-methylheptan-2-one can be industrially produced simply and efficiently.

That is, the present invention provides the following [1] to [11].

[1]. A method of producing an optically active (S)-2-methyl-6-oxoheptanoate, comprising allowing a R-body preferentially hydrolysable Aspergillus microorganism-derived esterase to act on a 2-methyl-6-oxoheptanoate of the formula (II):

(wherein, $R^1$ represents an alkyl group having 1 to 5 carbon atoms.) to cause optical resolution, thereby producing an optically active (S)-2-methyl-6-oxoheptanoate of the formula (III):

(wherein, $R^1$ represents the same meaning as described above.

[2]. The production method according to [1], further comprising a step of protecting a carbonyl group of the optically active (S)-2-methyl-6-oxoheptanoate of the formula (III):

(wherein, $R^1$ represents an alkyl group having 1 to 5 carbon atoms.)
to obtain an optically active (S)-ketal ester of the formula (IV):

(wherein, A represents an oxygen atom or sulfur atom, $R^1$ represents the same meaning as described above, and $R^2$ and $R^3$ represent each independently an alkyl group having 1 to 5 carbon atoms, or are mutually connected to represent an alkylene group having 2 to 5 carbon atoms.).

[3]. The production method according to [2], further comprising a step of reducing the optically active (S)-ketal ester of the formula (IV):

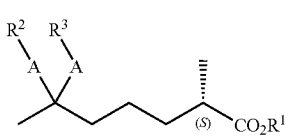

(wherein, A, $R^1$, $R^2$ and $R^3$ represent the same meanings as described above.)
to obtain an optically active (S)-ketal alcohol of the formula (V):

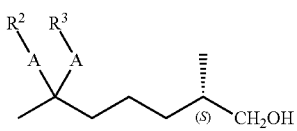

(wherein, A, $R^2$ and $R^3$ represent the same meanings as described above.).

[4]. A method of producing optically active (S)-7-hydroxy-6-methylheptan-2-one of the formula (I), comprising the steps of
allowing a R-body preferentially hydrolysable Aspergillus microorganism-derived esterase to act on a 2-methyl-6-oxoheptanoate of the formula (II):

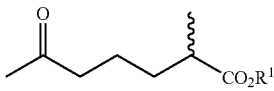

(wherein, $R^1$ represents the same meaning as described above.) to cause optical resolution, thereby producing an optically active (S)-2-methyl-6-oxoheptanoate of the formula (III):

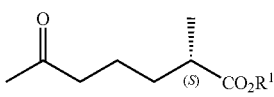

(wherein, $R^1$ represents the same meaning as described above.),
protecting a carbonyl group of the optically active (S)-2-methyl-6-oxoheptanoate of the formula (III) to obtain an optically active (S)-ketal ester of the formula (IV):

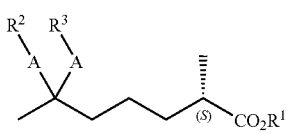

(wherein, A, $R^1$, $R^2$ and $R^3$ represent the same meanings as described above.),
reducing the optically active (S)-ketal ester of the formula (IV) to obtain an optically active (S)-ketal alcohol of the formula (V):

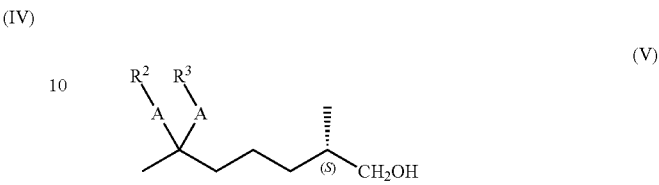

(wherein, A, $R^2$ and $R^3$ represent the same meanings as described above.), and
de-protecting the optically active (S)-ketal alcohol of the formula (V) to obtain optically active (S)-7-hydroxy-6-methylheptan-2-one of the formula (I):

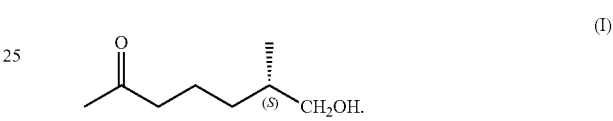

[5]. The production method according to any one of [1] to [4], wherein the optically active (S)-2-methyl-6-oxoheptanoate of the formula (III) has an optical purity of 95 to 100% ee.

[6]. The production method according to any one of [1] to [5], wherein $R^1$ is a methyl group.

[7]. The production method according to any one of [2] to [6], wherein $R^2$ and $R^3$ are all a methyl group or mutually connected to represent an ethylene group or propylene group.

[8]. The production method according to any one of [1] to [7], wherein the Aspergillus microorganism is Aspergillus flavus.

[9]. The production method according to any one of [1] to [8], wherein the Aspergillus microorganism is Aspergillus flavus ATCC11492 strain.

[10]. An optically active (S)-ketal ester of the formula (IV'):

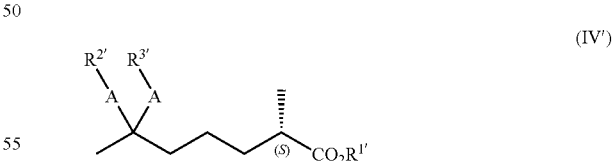

(wherein, A is an oxygen atom or sulfur atom, $R^{1\prime}$ is a methyl group, ethyl group, propyl group or butyl group, and $R^{2\prime}$ and $R^{3\prime}$ are all a methyl group, alternatively, A is an oxygen atom or sulfur atom, $R^{1\prime}$ is a methyl group, and $R^{2\prime}$ and $R^{3\prime}$ are mutually connected to represent an ethylene group or propylene group).

[11]. The optically active (S)-ketal ester according to [10], wherein A is an oxygen atom, and $R^{1\prime}$, $R^{2\prime}$ and $R^{3\prime}$ are all a methyl group.

MODES FOR CARRYING OUT THE INVENTION

The present invention will be described in detail below.

First, the definitions of groups used in the present specification will described below.

"An alkyl group having 1 to 5 carbon atoms" is a linear or branched alkyl group having 1 to 5 carbon atoms, and examples thereof include a methyl group, ethyl group, n-propyl group, isopropyl group, n-butyl group, isobutyl group, sec-butyl group, tert-butyl group, pentyl group, isopentyl group, neopentyl group, tert -pentyl group, 1,2-dimethylpropyl group and the like. Of them, preferable are a methyl group, ethyl group and n-propyl group, more preferable is a methyl group.

"An alkylene group having 2 to 5 carbon atoms" is a linear or branched alkylene group having 2 to 5 carbon atoms, and examples thereof include an ethylene group, propylene group, butylene group, pentylene group and the like. Preferable are an ethylene group and propylene group.

$R^1$ is preferably a methyl group, ethyl group or n-propyl group, more preferably a methyl group.

$R^2$ and $R^3$ are preferably all a methyl group or mutually connected to form an ethylene group or propylene group.

In the present invention, a R-body preferentially hydrolysable Aspergillus microorganism-derived esterase is allowed to act on a 2-methyl-6-oxoheptanoate of the above-described formula (II) (hereinafter, referred to also as 2-methyl-6-oxoheptanoate (II)), to produce an optically active (S)-2-methyl-6-oxoheptanoate of the above-described formula (III) (hereinafter, referred to also as (S)-2-methyl-6-oxoheptanoate (III)) (step a).

The 2-methyl-6-oxoheptanoate (II) includes two kinds of optical isomers (S body and R body) containing as an asymmetrical center a carbon atom at α-position of a $-CO_2R^1$ group, and the 2-methyl-6-oxoheptanoate (II) used in the production method of the present invention may be a racemate containing these optical isomers in equal amount, or a mixture containing one optical isomer in excess amount (at any proportion). A racemate is preferable. The wavy line in the formula (II) represents a single bond to a methyl group, meaning that the 2-methyl-6-oxoheptanoate (II) is the above-described racemate or the above-described mixture containing one optical isomer in excess amount (at any proportion), around the carbon atom to which a methyl group bonds, as an asymmetrical center.

The 2-methyl-6-oxoheptanoate (II) can be obtained, for example, by esterifying 2-methyl-6-oxoheptanoic acid, referring to descriptions in the above-described patent documents 1, 2, 7, non-patent documents 1, 2, and the like. This 2-methyl-6-oxoheptanoic acid can be obtained, for example, by oxidizing industrially easily available 2,6-dimethylcyclohexanone using potassium permanganate, referring to non-patent documents 7, 8, and the like.

The esterase to be used in the step a is capable of hydrolyzing preferentially a R-body. In the present invention, R-body preferentially hydrolysable Aspergillus microorganism-derived esterase (hereinafter, also referred to simply as esterase) is used, preferably, R-body preferentially hydrolysable Aspergillus flavus-derived esterase, more preferably, Aspergillus flavus ATCC11492 strain-derived esterase is used. These esterases may be esterases produced by recombinant microorganisms transformed by introduction of an enzyme gene contained in these microorganisms, esterases derived from mutants derived from these microorganisms by a mutagenic agent or treatment with ultraviolet ray or the like, or mutated esterases obtained by deletion, addition or substitution of one or more specific amino acids in an amino acid sequence in these esterases by a gene engineering means.

Microorganisms producing these esterases can be liquid-cultured by a usual method.

As a medium, various media appropriately containing carbon sources, nitrogen sources, inorganic substances and the like usually used in microorganism culture can be used. Examples of the carbon source include glucose, glycerol, organic acids, molasses and the like. Examples of the nitrogen source include peptone, yeast extract, malt extract, soy bean powder, corn steep liquor, cotton seed powder, dry yeast, casamino acid, amino acids, ammonium chloride, ammonium nitrate, ammonium sulfate, urea and the like.

The inorganic substance includes hydrochlorides of metals such as potassium, sodium, magnesium, iron, manganese, cobalt, zinc and the like, sulfates of the above-described metals, and phosphates of the above-described metals. More specifically, potassium chloride, sodium chloride, magnesium sulfate, ferrous sulfate, manganese sulfate, cobalt chloride, calcium chloride, zinc sulfate, potassium phosphate, sodium phosphate and the like.

For enhancing asymmetric hydrolysis ability of the above-described microorganism, olive oil or triglycerides such as tributyrin and the like, or the above-described substrates may be added appropriately to a medium.

Culture is usually carried out advantageously in an aerobic atmosphere, and shaking culture or stirring culture under ventilation is preferable. The culture temperature is usually in the range of about 20 to about 40° C., preferably in the range of 25 to 35° C. pH is preferably in the range of 6 to 8. The culture time varies depending on the conditions, and is preferably in the range of 1 to 7 days.

Solid culture methods can also be adopted, providing a microorganism fungus body having an asymmetric hydrolysis ability of the above-described substrate is obtained in these methods.

As a method of purifying the above-described enzyme from a microorganism culture cultured as described above, methods generally adopted in enzyme purification can be adopted.

For example, first, a fungus body in a microorganism culture is fractured by a method such as ultrasound treatment, dynau mill treatment, French press treatment or the like. Then, insoluble components are removed from the resultant fractured liquid by centrifugal separation and the like, then, an intended enzyme can be purified by one of, or an appropriate combination of two or more of cation exchange column chromatography, anion exchange column chromatography, hydrophobic column chromatography, gel filtration column chromatography and the like, usually used for enzyme purification.

Examples of carriers used in these column chromatography means include DEAE-Sepharose fastflow (manufactured by Amersham Pharmacia Biotech), Butyl-Toyopearl 650S (manufactured by Tosoh Corp.) and the like.

The shape of the esterase is not particularly restricted, and various shapes can be used such as purified esterase, coarse esterase, esterase-containing material, microorganism culture liquid, microorganism culture, fungus body, fungus body culture liquid, and materials obtained by treating them, and the like, and from the standpoint of providing an industrial production method, it is preferable to use those obtained by immobilization of esterases of various shapes as described above. The immobilization method includes those immobilizing the esterase onto, for example, an inorganic carrier such as silica gel, ceramics and the like, a natural resin such as cellulose and the like, or a synthetic resin such as a styrenedivinylbenzene copolymer and the like by using a known method such as an adsorption method, polyacrylamide method, sulfur-containing polysaccharide gel method, alginic acid gel method, agar gel method and the like. Of them, esterases immobilized by an adsorption method are preferably used.

The use amount of the esterase may be advantageously selected appropriately so that hydrolysis progresses with good stereoselectivity, depending on the esterase shape, enzyme activity and the like. For example, when the esterase is in the shape of purified esterase or coarse esterase, the use amount thereof is usually in the range of 0.001 to 2 parts by weight, preferably in the range of 0.002 to 0.5 parts by weight with respect to 1 part by weight of a 2-methyl-6-oxoheptanoate (II). In the case of the shape of microorganism culture, fungus body and treated material thereof, the use amount thereof is usually in the range of 0.01 to 200 parts by weight, preferably in the range of 0.1 to 50 parts by weight with respect to 1 part by weight of a 2-methyl-6-oxoheptanoate (II).

Hydrolysis with an esterase is carried out in water or a mixed solvent of water and an organic solvent. The use amount of water is usually 0.5 to 200 parts by weight, preferably 0.5 to 20 parts by weight with respect to 1 part by weight of a 2-methyl-6-oxoheptanoate (II).

The organic solvent includes hydrophobic organic solvents and hydrophilic organic solvents, and examples of the hydrophobic organic solvent include ethers such as methyl t-butyl ether, isopropyl ether and the like; ketones such as methyl isobutyl ketone, methyl ethyl ketone and the like; hydrocarbons such as toluene, hexane, cyclohexane, heptanes and the like. Examples of the hydrophilic organic solvent include alcohols such as t-butanol, methanol, ethanol, isopropanol, n-butanol and the like; ethers such as tetrahydrofuran and the like; sulfoxides such as dimethyl sulfoxide and the like; ketones such as acetone and the like; amides such as N,N-dimethylformamide and the like; nitriles such as acetonitrile, and the like. These hydrophobic organic solvents and hydrophilic organic solvents may each be used singly or in combination of two or more, alternatively, the hydrophobic organic solvents and hydrophilic organic solvents may be combined.

The use amount of the organic solvent is usually 200 parts by weight or less, preferably 0.1 to 100 parts by weight with respect to 1 part by weight of a 2-methyl-6-oxoheptanoate (II).

Hydrolysis with an esterase is carried out while maintaining pH at a value at which the stereoselectivity of hydrolysis does not lower, usually, pH 4 to 10, preferably pH 6 to 8, depending on the kind of the esterase.

For regulating pH in the above-described range, a buffered aqueous solution is used, and examples of the buffered aqueous solution include buffered aqueous solutions of inorganic acid salts such as aqueous solutions of alkali metal phosphates (sodium phosphate aqueous solution, potassium phosphate aqueous solution and the like) and so forth, buffered aqueous solutions of organic acid salts such as aqueous solutions of alkali metal acetates (sodium acetate aqueous solution, potassium acetate aqueous solution and the like) and so forth. The concentration of this buffering liquid is preferably 0.01 to 0.3 M, more preferably 0.05 to 0.1 M. This buffering liquid acts also as a solvent.

For maintaining pH in the above-described range, if necessary, a base may be added to the reaction system to control it. Examples of the base include alkali metal hydroxides such as sodium hydroxide, potassium hydroxide and the like, alkali metal carbonates such as sodium carbonate, potassium carbonate and the like, alkaline earth metal carbonates such as calcium carbonate and the like; alkali metal bicarbonates such as sodium hydrogen carbonate, potassium hydrogen carbonate and the like, phosphates such as sodium dihydrogen phosphate, disodium hydrogen phosphate, potassium dihydrogen phosphate, dipotassium hydrogen phosphate and the like; organic bases such as triethylamine, pyridine and the like; ammonia, and the like. These bases may be used singly, or in admixture of two or more. The base is usually added in the form of aqueous solution, and it may also be added in the form of solution of a mixed solvent of an organic solvent and water. As this organic solvent, the same solvents as described above are mentioned. Further, the base may be added in the form of solid, or may be added in the form of suspension.

The hydrolysis method is not particularly restricted, and for example, methods of mixing water (for example, buffered aqueous solution), 2-methyl-6-oxoheptanoate (II) and esterase (for example, those immobilized onto resin and the like) are mentioned. In the case of use of an organic solvent, water, 2-methyl-6-oxoheptanoate (II) and esterase may be advantageously mixed in the organic solvent.

The reaction temperature is preferably in the range of about 5 to 65° C., more preferably in the range of about 10 to 50° C. The reaction time is usually 1 to 100 hours, varying depending on the reaction temperature. When the reaction temperature is over 65° C., the stability of an esterase tends to lower, and when lower than 5° C., the reaction speed tends to lower.

By the above-described hydrolysis, a R body in a 2-methyl-6-oxoheptanoate (II) is hydrolyzed stereoselectively into a carboxylic acid while maintaining its steric configuration (that is, optically active (R)-2-methyl-6-oxoheptanoic acid is generated).

Thus, a reaction mixture containing an unreacted optically active (S)-2-methyl-6-oxoheptanoate (II) and its hydrolysate optically active (R)-2-methyl-6-oxoheptanoic acid is obtained.

For separating these compounds in the reaction mixture, or for separating the esterase, buffering agent (constituent component in buffered aqueous solution) and the like used in the reaction from these compounds, a post treatment operation may be further carried out. Examples of the post treatment operation include a method of distilling off a solvent in the reaction mixture before separation and purification using silica gel chromatography, a method of separation and purification by a liquid-partitioning operation, and the like. Specifically, the reaction mixture after hydrolysis can be subjected to, for example, a treatment as described below to isolate an optically active (S)-2-methyl-6-oxoheptanoate (II). First, when an esterase, immobilization carrier and the like which are insoluble in the reaction mixture are present, the reaction mixture is filtrated through a filtration aid if necessary, to remove these insoluble materials. Here, for improving filterability, a heat modification or acid modification treatment may be performed on the esterase, or body feed filtration (reaction mixture is mixed with filtration aid and subjected to filtration) may be carried out. Then, if necessary, pH of the filtrate is controlled to 6 to 9, then, the filtrated is partitioned into an aqueous layer and an organic layer, obtaining a solution of an optically active (S)-2-methyl-6-oxoheptanoate (III) as the organic layer. Here, for improving liquid-partitioning property, alcohols such as methanol, ethanol, n-butanol and the like may be added to the filtrate. In the case of use of a hydrophobic organic solvent in hydrolysis, the resultant reaction mixture may be itself partitioned, however, when no hydrophobic organic solvent is used in hydrolysis, when partitioning cannot be carried out easily due to small use amount thereof, or when partitioning cannot be carried out easily due to small use amount of water, and the like, it may be permissible to perform liquid-partitioning after appropriately adding a hydrophobic organic solvent, water and the like. Examples of the hydrophobic organic solvent include ethers such as methyl t-butyl ether, isopropyl ether and the like, hydrocarbons such as toluene, hexane, cyclohexane, heptanes and the like, halogenated hydrocarbons such as dichloromethane, dichloroethane, chloroform, chlorobenzene, orthodichlorobenzene and the like, ketones such as methyl ethyl ketone, methyl isobutyl ketone and the like, esters such as ethyl acetate, methyl acetate, butyl acetate, and the like.

Then, by distilling off an organic solvent from the resultant organic solvent solution of optically active (S)-2-methyl-6-oxoheptanoate (III), an intended optically active (S)-2-methyl-6-oxoheptanoate (III) can be taken out. The resultant optically active (S)-2-methyl-6-oxoheptanoate (III) may be further purified by distillation, column chromatography and the like.

A hydrolysate, optically active (R)-2-methyl-6-oxoheptanoic acid is contained in an aqueous layer after liquid-partitioning, and this can be taken out easily from the aqueous layer by distilling off water, or extracting using an organic solvent after a neutralization treatment, and the like. The resultant optically active (R)-2-methyl-6-oxoheptanoic acid can be subjected to treatments of esterification and racemization, to attain recycle as a 2-methyl-6-oxoheptanoate (II).

Thus obtained optically active (S)-2-methyl-6-oxoheptanoate (III) has an optical purity of preferably 90 to 100% ee, more preferably 95 to 100% ee, most preferably 98 to 100% ee.

This optically active (S)-2-methyl-6-oxoheptanoate (III) can be induced into an intended optically active (S)-7-hydroxy-6-methylheptan-2-one (I) by the following steps b to d.

(Step b)

This step is an step of protecting a carbonyl group of an optically active (S)-2-methyl-6-oxoheptanoate(III), to obtain an optically active (S)-ketal ester of the above-described formula (IV) (hereinafter, also referred to as optically active (S)-ketal ester (IV)). In the present invention, the optically active (S)-ketal ester (IV) includes an optically active (S)-thioketal ester.

The method of protecting a carbonyl group is not particularly restricted, and any methods usually used in the art for converting a carbonyl group into a ketal group (A=O) or a thioketal group (A=S) (that it, protecting carbonyl group) can be adopted. For example, a method of reacting an optically active (S)-2-methyl-6-oxoheptanoate (III) with alcohols or orthoformate or thiols corresponding to $R^2$ and $R^3$ in an organic solvent in the presence of an acid catalyst is mentioned.

The organic solvent is not particularly restricted providing it does not disturb the progress of the reaction, and examples thereof include ethers such as tert-butyl methyl ether, isopropyl ether and the like; hydrocarbons such as toluene, hexane, cyclohexane, heptane, octane, isooctane and the like; halogenated hydrocarbons such as dichloromethane, dichloroethane, chloroform, chlorobenzene, orthodichlorobenzene, and the like. The use amount of the organic solvent may be appropriately adjusted depending on the kind of an optically active (S)-2-methyl-6-oxoheptanoate (III), and usually 0.5 to 50 parts by weight with respect to 1 part by weight of the optically active (S)-2-methyl-6-oxoheptanoate (III).

The acid catalyst is not particularly restricted, and examples thereof include inorganic acids such as hydrochloric acid, ammonium chloride and the like; organic acids such as camphorsulfonic acid, p-toluenesulfonic acid monohydrate and the like; strongly acidic ion exchange resins such as Amberlyst and the like. The use amount of the acid catalyst is preferably 0.001 to 0.5 equivalents, more preferably 0.005 to 0.2 equivalents with respect to 1 equivalent of an optically active (S)-2-methyl-6-oxoheptanoate (III).

The alcohols corresponding to $R^2$ and $R^3$ are not particularly restricted, and examples thereof include methanol, ethanol, ethylene glycol, 1,3-propanediol, 2,2-dimethyl-1,3-propanediol and the like. The use amount of the alcohols is preferably 1 to 50 equivalents, more preferably 2 to 10 equivalents with respect to 1 equivalent of an optically active (S)-2-methyl-6-oxoheptanoate (III).

The orthoformate corresponding to $R^2$ and $R^3$ is not particularly restricted, and examples thereof include methyl orthoformate, ethyl orthoformate, propyl orthoformate and the like. The use amount of the orthoformate is preferably 1 to 50 equivalents, more preferably 2 to 10 equivalents with respect to 1 equivalent of an optically active (S)-2-methyl-6-oxoheptanoate (III).

The thiols corresponding to $R^2$ and $R^3$ are not particularly restricted, and examples thereof include methanethiol, ethanethiol, propanethiol, isopropanethiol, butanethiol, 1,2-ethanedithiol, 1,3-propanedithiol and the like. The use amount of the thiols is preferably 1 to 50 equivalents, more preferably 2 to 10 equivalents with respect to 1 equivalent of an optically active (S)-2-methyl-6-oxoheptanoate (III), and optionally, it may also be the solvent amount.

The reaction temperature is preferably 10 to 120° C., more preferably 20 to 60° C. The reaction time varies depending on the reaction temperature, and usually is from 10 minutes to 50 hours.

The reaction mixture obtained in the above-described reaction can be subjected, for example, to a liquid-partitioning operation and the like, to isolate an optically active (S)-ketal ester (IV). The isolated optically active (S)-ketal ester (IV) can be purified, if necessary, by conventional means such as distillation, chromatography and the like.

(Step c)

This step is a step of reducing an optically active (S)-ketal ester (IV) to obtain an optically active (S)-ketal alcohols of the above-described formula (V) (hereinafter, also referred to as optically active (S)-ketal alcohol (V)). In the present invention, the optically active (S)-ketal alcohol (V) includes an optically active (S)-thioketal alcohol.

The reducing method is not particularly restricted, and any methods usually used in the art for reducing a carboxylate into an alcohol can be adopted. For example, a method of reacting an optically active (S)-ketal ester (IV) with a reducing agent in an organic solvent is mentioned.

The organic solvent is not particularly restricted providing it does not disturb the progress of the reaction, and examples thereof include ethers such as diethyl ether, diisopropyl ether, tetrahydrofuran (THF), 1,4-dioxane, tert-butyl methyl ether and the like; hydrocarbons such as hexane, heptane, toluene and the like; halogenated hydrocarbons such as dichloromethane, dichloroethane, chlorobenzene, orthodichlorobenzene, and the like. The use amount of the organic solvent may be appropriately adjusted depending on the kind of an optically active (S)-ketal ester(IV), and usually 1 to 100 parts by weight with respect to 1 part by weight of the optically active (S)-ketal ester(IV).

As the reducing agent, those reducing an ester to give an alcohol are usually used. Examples thereof include alkali metal borohydrides such as sodium borohydride, lithium borohydride and the like; alkali metal trialkylborohydrides such as lithium triethylborohydride and the like; alkali metal aluminum hydrides such as lithium aluminum hydride and the like; dialkylaluminum hydrides such as diisobutylaluminum hydride and the like; etc. The use amount of the reducing agent is preferably 0.5 to 20 equivalents, more preferably 1 to 10 equivalents with respect to 1 equivalent of an optically active (S)-ketal ester (IV).

The reaction temperature is preferably −78 to 60° C., more preferably −40 to 30° C. The reaction time varies depending on the reaction temperature, and is usually 1 to 70 hours.
(Step d)

This step is a step of de-protecting an optically active (S)-ketal alcohol (V) to obtain an optically active (S)-7-hydroxy-6-methylheptan-2-one of the above-described formula (I) (hereinafter, also referred to as optically active (S)-7-hydroxy-6-methylheptan-2-one (I)).

The de-protecting method is not particularly restricted, and any methods usually used in the art for de-protecting the carbonyl group protected in the step b (namely, converting the ketal group (A=O) or thioketal group (A=S) into a carbonyl group) can be adopted. For example, a method of performing an acid treatment in water or an organic solvent is mentioned.

The organic solvent is not particularly restricted providing it does not disturb the progress of the reaction, and examples thereof include alcohols such as methanol, ethanol and the like; ethers such as diethyl ether, diisopropyl ether, tetrahydrofuran (THF), 1,4-dioxane, tert-butyl methyl ether and the like; halogenated hydrocarbons such as dichloromethane, dichloroethane, chloroform, chlorobenzene, orthodichlorobenzene and the like; ketones such as acetone and the like; hydrocarbons such as toluene, hexane, cyclohexane, heptane, octane, isooctane and the like; and mixed solvents thereof, and the like. The use amount of the organic solvent may be appropriately adjusted depending on the kind of an optically active (S)-ketal alcohol (V), and usually 2 to 50 parts by weight with respect to 1 part by weight of the optically active (S)-ketal alcohol (V). These organic solvents may be each used singly or in admixture with water.

The acid is not particularly restricted, and examples thereof include inorganic acids such as hydrochloric acid, sulfuric acid, phosphoric acid and the like; organic acids such as trifluoroacetic acid, p-toluenesulfonic acid, formic acid, acetic acid, oxalylic acid and the like; strongly acidic ion exchange resins such as Amberlyst and the like. The use amount of the acid is preferably 0.001 to 50 equivalents, more preferably 0.1 to 10 equivalents with respect to 1 equivalent of an optically active (S)-ketal alcohol (V).

The reaction temperature is preferably 0 to 100° C., more preferably 20 to 80° C. The reaction time varies depending on the reaction temperature, and usually is from 30 minutes to 24 hours.

In the case of a thioketal group (A=S), there is also a method of using a reaction reagent such as metal salts, oxidizers, halogenating agents and the like, and this method is preferable from the standpoint of reactivity.

The metal salt includes silver salts such as silver (I) perchlorate, silver oxide, silver nitrate and the like; mercury salts such as mercury chloride, mercury oxide and the like; thallium salts such as thallium (III) nitrate, thallium (III) trifluoroacetate and the like; copper salts such as copper (I) chloride, copper (I) oxide and the like. The oxidizer includes 2,3-dichloro-5,6-dicyano-p-benzoquinone (DDQ), m-chloroperbenzoic acid (mCPBA), cerium ammonium nitrile, sodium periodate, hydrogen peroxide, molecular oxygen and the like. The halogenating agent includes iodine, N-bromosuccinimide, N-chlorosuccinimide and the like. The use amount of these reaction reagents is preferably 1 to 20 equivalents, more preferably 1 to 10 equivalents with respect to 1 equivalent of an optically active (S)-ketal alcohol (V).

Used as the reaction solvent are organic solvents, or mixed solvents of organic solvents with water. The organic solvent is not particularly restricted providing it does not disturb the progress of the reaction, and examples thereof include alcohols such as methanol, ethanol and the like; ethers such as diethyl ether, diisopropyl ether, tetrahydrofuran (THF), 1,4-dioxane, tert-butyl methyl ether and the like; halogenated hydrocarbons such as dichloromethane, dichloroethane, chloroform, chlorobenzene, orthodichlorobenzene and the like; ketones such as acetone and the like; hydrocarbons such as toluene, hexane, cyclohexane, heptanes, octane, isooctane and the like; and mixed solvents thereof, and the like. The use amount of the organic solvent may be appropriately adjusted depending on the kind of an optically active (S)-ketal alcohol (V), and usually 1 to 100 parts by weight with respect to 1 part by weight of the optically active (S)-ketal alcohol (V).

The reaction temperature is preferably −45 to 160° C., more preferably 0 to 80° C. The reaction time varies depending on the reaction temperature, and is usually from 5 minutes to 20 hours.

Thus obtained optically active (S)-7-hydroxy-6-methylheptan-2-one (I) can be purified, if necessary, by conventional means such as distillation, chromatography and the like. The steps b to d may be carried out independently as separate steps, or as continuous single steps.

Instead of the step a and the step b, the following steps A and B may be carried out.

Step A: of protecting a carbonyl group of a 2-methyl-6-oxoheptanoate (II) to obtain a ketal ester of the formula (VI):

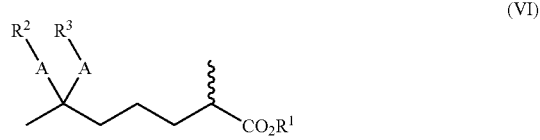

(wherein, A, $R^1$, $R^2$ and $R^3$ are as defined above.)
(hereinafter, also referred to as ketal ester(VI)), and Step B: of allowing a R-body preferentially hydrolysable Aspergillus microorganism-derived esterase to act on a ketal ester (VI) to obtain an optically active (S)-ketal ester (IV).

The step A can be carried out by the same method as for the step b. The step B can be carried out by the same method as for the step a.

Of optically active (S)-ketal esters (IV), compounds of the formula (IV'):

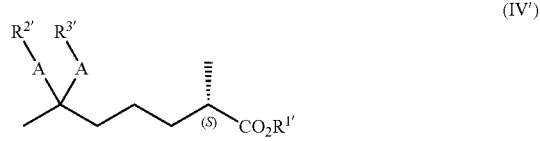

(wherein, A is an oxygen atom or sulfur atom, $R^{1'}$ is a methyl group, ethyl group, propyl group or butyl group and $R^{2'}$ and $R^{3'}$ are all a methyl group, alternatively, A is an oxygen atom or sulfur atom, $R^{1'}$ is a methyl group and $R^{2'}$ and $R^{3'}$ are mutually connected to from an ethylene group or propylene group.) are novel compounds. Optically active (S)-ketal alcohols (V) are also novel compounds.

According to the production method of the present invention, an optically active (S)-7-hydroxy-6-methylheptan-2-one (I) and its precursor optically active (S)-2-methyl-6-oxoheptanoate (III) can be industrially produced simply and efficiently.

EXAMPLES

The present invention will be illustrated further in detail below based on examples, but it is needless to say that the present invention is not limited to these examples.

Reference Example 1

Synthesis of racemate of 2-methyl-6-oxoheptanoic acid (No. 1)

A suspension of potassium permanganate (195.7 g, 1.24 mol) in water (1390 ml) was added carefully to a mixture of 2,6-dimethylcyclohexanone (120.0 g, 0.95 mol) and water (600 ml) while stirring vigorously the mixture at 30° C. or lower over a period of about 1 hour, and the mixture was stirred at room temperature overnight. The produced manganese dioxide was filtrated, and the filtration cake was washed with methyl tert-butyl ether (250 ml) and water (250 ml). The organic layer of the filtrate was separated, and the aqueous layer was adjusted to pH 1.0 with 35% concentrated hydrochloric acid (about 150 ml), and sodium chloride (400 g) was added and the mixture was extracted with ethyl acetate (300 ml×5), and the organic layer was dried over anhydrous magnesium sulfate, then, the solvent was distilled off under reduced pressure, and the resultant residual oil was distilled under reduced pressure by a vacuum pump. Fractions of boiling points of 130 to 144° C./267 Pa were collected, to obtain 79.92 g (yield 53.2%) of a racemate of 2-methyl-6-oxoheptanoic acid.

Reference Example 2

Synthesis of 2-methyl-6-oxoheptanoic acid (No. 2)

2,6-dimethylcyclohexanone (93.0 g, 0.737 mol), water (1057 ml) and acetone (333 ml) were charged in a 2 L colben, and heated up to an inner temperature of 50° C. with a hot water bath. Potassium permanganate (326 g, 2.06 mol) was divided into 9 portions and added at 45 to 55° C. while stirring. The mixture was stirred at the same temperature for about 2 hours. At the same temperature, the produced manganese dioxide was filtrated using a Buchner funnel having a diameter of 12 cm, and materials remaining on the funnel were washed out with water (300 ml) and acetone (100 ml). The filtrate was stirred at a bath temperature of 40° C. under reduced pressure of 14.7 to 17.3 kPa to distill acetone off.

Sodium chloride (330 g) was added and dissolved in thus obtained aqueous solution, and washed with ethyl acetate (200 ml). It was further was washed with THF (200 ml), then, THF (500 ml) was added, and 35% synthetic hydrochloric acid (107 ml) was dropped to make the aqueous solution acidic from pH 8.7 to pH 0.81. After partitioning into the THF layer and the aqueous layer, the aqueous layer was further extracted with THF (150 ml), and combined with the initial THF layer.

To the resultant THF solution was added magnesium chloride (4.0 g) and the mixture was stirred for 30 minutes. The aqueous layer separating from the THF layer was partitioned and removed. Thereafter, THF was distilled off under reduced pressure at a bath temperature of 40° C., further, evacuated for 60 minutes by a vacuum pump (133 Pa) at a bath temperature of 50° C. while stirring by a magnetic stirrer, to obtain 106.27 g of a racemate of 2-methyl-6-oxoheptanoic acid (content 93.9% (gas chromatography (GC); with respect to distilled product), purity-reduced yield 85.7%).

Reference Example 3

Synthesis of racemate of 2-methyl-6-oxoheptanoic acid methyl ester 43 g of a racemate of 2-methyl-6-oxoheptanoic acid (purity 99.65%, 0.27mmol) was dissolved in214.25 g of methanol, then, 2.14 g of concentrated sulfuric acid was added and mixed. Next, the mixture was heated up to 65° C., then, reacted for 5 hours at the same temperature. After completion of the reaction, the reaction mixture was cooled down to room temperature. Next, the reaction mixture was concentrated under reduced pressure until reaching about one-forth of the original weight, then, 30 g of water was added. Further, 128.55 g of methyl t-butyl ether (MTBE) was added, then, 55.06 g of a 5% sodium hydrogen carbonate aqueous solution was dropped at room temperature while stirring. The resultant mixture was stirred sufficiently at room temperature, then, liquid-partitioned, and the aqueous layer was further partitioned with 64.27 g of MTBE. The resultant organic layer was combined, and concentrated under reduced pressure, to obtain 45.4 g (content 94.3%, yield 92%) of a coarse product of a racemate of 2-methyl-6-oxoheptanoic acid methyl ester as colorless oil. The resultant coarse product was used as it is in the subsequent reaction (the resultant coarse product may be, if necessary, distilled (boiling point 107° C./1333 Pa), then, used in the next reaction).

Example 1

Optical resolution of racemate of 2-methyl-6-oxoheptanoic acid methyl ester by hydrolysis using Aspergillus flavus ATCC11492 strain-derived esterase (No. 1)

1.0 g (5.75 mmol) of a racemate of 2-methyl-6-oxoheptanoic acid methyl ester was suspended in 5.0 g of 0.1 M phosphoric acid buffered solution (pH 7.0). The suspension was cooled to 10° C., then, 0.7 g (moisture percentage 56%, enzymatic activity 4028 KU/Kg, reduced by dry product) of immobilized Aspergillus flavus ATCC11492 strain-derived esterase (prepared by a method described in JP-A No. 2003-70471) was added, and the mixture was stirred at 10° C. for 23 hours while maintaining pH at 6 to 7 by appropriately adding 4% NaOH aqueous solution. Thereafter, a part of the reaction solution was taken out, and analyzed by HPLC [Chiralpak AS-H, 4.6 mm×25 cm (manufactured by Daicel Chemical Industries, Ltd.)], and the optical purity and the reaction yield of the optically active (S)-2-methyl-6-oxoheptanoic acid methyl ester were measured. As a result, the optical purity was 100% ee, and the reaction yield was 47% (value calculated from the optical purity).

As reference, a hydrolysate optically active (R)-2-methyl-6-oxoheptanoic acid had an optical purity of 90.4% ee and a reaction yield of 52.5% (value calculated from the optical purity).

Example 2

Optical resolution of racemate of 2-methyl-6-oxoheptanoic acid methyl ester by hydrolysis using Aspergillus flavus ATCC11492 strain-derived esterase (No. 2)

1.0 g (5.75 mmol) of a racemate of 2-methyl-6-oxoheptanoic acid methyl ester and 2.0 g of methyl t-butyl ether (MTBE) were suspended in 5.0 g of 0.1 M phosphoric acid buffered solution (pH 7.0). The suspension was cooled to 10° C., then, 0.7 g (moisture percentage 56%, enzymatic activity 4028 KU/Kg, reduced by dry product) of immobilized Aspergillus flavus ATCC11492 strain-derived esterase (prepared by a method described in JP-A No. 2003-70471) was added, and the mixture was stirred at 10° C. for 23 hours while maintaining pH at 6 to 8 by appropriately adding 4% NaOH aqueous solution. Thereafter, a part of the reaction solution was taken out, and analyzed by HPLC [Chiralpak AS-H, 4.6 mm×25 cm (manufactured by Daicel Chemical Industries, Ltd.)], and the optical purity and the reaction yield of the optically active (S)-2-methyl-6-oxoheptanoic acid methyl ester were measured. As a result, the optical purity was 100% ee, and the reaction yield was 47% (value calculated from the optical purity).

As reference, a hydrolysate optically active (R)-2-methyl-6-oxoheptanoic acid had an optical purity of 88.2% ee and a reaction yield of 53% (value calculated from the optical purity).

Example 3

Optical resolution of racemate of 2-methyl-6-oxoheptanoic acid methyl ester by hydrolysis using Aspergillus flavus ATCC11492 strain-derived esterase (No. 3)

1.0 g (5.75 mmol) of a racemate of 2-methyl-6-oxoheptanoic acid methyl ester and 2.0 g of MTBE were suspended in 5.0 g of 0.1 M phosphoric acid buffered solution (pH 7.0). The suspension was cooled to 10° C., then, 0.1 g (moisture percentage 56%, enzymatic activity 4028 KU/Kg, reduced by dry product) of immobilized Aspergillus flavus ATCC11492 strain-derived esterase (prepared by a method described in JP-A No. 2003-70471) was added, and the mixture was stirred at 10° C. for 99 hours while maintaining pH at 6 to 8 by appropriately adding 4% NaOH aqueous solution. Thereafter, a part of the reaction solution was taken out, and analyzed by HPLC [Chiralpak AS-H, 4.6 mm×25 cm (manufactured by Daicel Chemical Industries, Ltd.)], and the optical purity and the reaction yield of the optically active (S)-2-methyl-6-oxoheptanoic acid methyl ester were measured. As a result, the optical purity was 99.8% ee, and the reaction yield was 48.5% (value calculated from the optical purity).

As reference, a hydrolysate optically active (R)-2-methyl-6-oxoheptanoic acid had an optical purity of 94.2% ee and a reaction yield of 51.5% (value calculated from the optical purity).

Example 4

Optical resolution of racemate of 2-methyl-6-oxoheptanoic acid methyl ester by hydrolysis using Aspergillus flavus ATCC11492 strain-derived esterase (No. 4)

10.6 g (content 94.3%, 5.75 mmol) of a racemate of 2-methyl-6-oxoheptanoic acid methyl ester and 20.0 g of MTBE were suspended in 50.0 g of 0.1 M phosphoric acid buffered solution (pH 7.0). The suspension was cooled to 10° C., then, 2.0 g (moisture percentage 56%, enzymatic activity 4028 KU/Kg, reduced by dry product) of immobilized Aspergillus flavus ATCC11492 strain-derived esterase (prepared by a method described in JP-A No. 2003-70471) was added, and the mixture was stirred at 10° C. for 51 hours while maintaining pH at 7.0 to 7.5 by appropriately adding 4% NaOH aqueous solution. Thereafter, the reaction solution was filtrated using Radiolite (filtration aid, trade name: manufactured by Showa Chemical Industry Co., Ltd.), to remove the esterase. The resultant filtrate was extracted twice with 25 g and 12.5 g of methyl isobutyl ketone (MIBK), then, the resultant organic layers were combined and washed with 15% saline, to obtain a MIBK solution of optically active (S)-2-methyl-6-oxoheptanoic acid methyl ester (optical purity 98.9% ee, yield 41.5%). The optical purity was analyzed by HPLC [Chiralpak AS-H, 4.6 mm×25 cm (manufactured by Daicel Chemical Industries, Ltd.)] like in Example 1.

Example 5

Optical resolution of racemate of 2-methyl-6-oxoheptanoic acid methyl ester by hydrolysis using Aspergillus flavus ATCC11492 strain-derived esterase (No. 5)

10.6 g (content 94.3%, 5.75 mmol) of a racemate of 2-methyl-6-oxoheptanoic acid methyl ester and 20.0 g of MTBE were suspended in 50.0 g of 0.1 M phosphoric acid buffered solution (pH 7.0). The suspension was cooled to 10° C., then, 2.0 g (moisture percentage 56%, enzymatic activity 4028 KU/Kg, reduced by dry product) of immobilized Aspergillus flavus ATCC11492 strain-derived esterase (prepared by a method described in JP-A No. 2003-70471) was added, and the mixture was stirred at 10° C. for 48 hours while maintaining pH at 7.5 to 8.0 by appropriately adding 4% NaOH aqueous solution. Thereafter, the reaction solution was filtrated using Radiolite (filtration aid, trade name: manufactured by Showa Chemical Industry Co., Ltd.), to remove the esterase. The resultant filtrate was extracted twice with 25 g and 12.5 g of MIBK, then, the resultant organic layers were combined and washed with 15% saline, to obtain a MIBK solution of optically active (S)-2-methyl-6-oxoheptanoic acid methyl ester (optical purity 98.8% ee, yield 40.3%). The optical purity was analyzed by HPLC [Chiralpak AS-H, 4.6 mm×25 cm (manufactured by Daicel Chemical Industries, Ltd.)] like in Example 1.

Reference Example 4

Synthesis of 6,6-dimethoxy-2-methylheptanoic acid methyl ester 15.4 g (content 84.4%, 75.5 mmol) of 2-methyl-6-oxoheptanoic acid methyl ester was dissolved in 24.2 g (0.75 mol) of methanol, then, 40.1 g (0.38 mol) of methyl orthoformate and 0.14 g (0.75 mmol) of p-toluenesulfonic acid monohydrate were added and mixed. Then, the mixture was heated up to 65° C. and reacted at the same temperature for 1.5 hours. After completion of the reaction, the reaction mixture was cooled down to room temperature. Next, to the reaction mixture was added 39 g of toluene and 26 g of a 3% sodium hydrogen carbonate aqueous solution and the mixture was stirred sufficiently. The reaction mixture was liquid-partitioned, then, the resultant organic layer was concentrated under reduced pressure, to obtain 22.8 g (content 69.5%, reaction yield 95%) of a coarse product of 6,6-dimethoxy-2-methylheptanoic acid methyl ester. The resultant coarse product of 6,6-dimethoxy-2-methylheptanoic acid methyl ester was used as it is in the subsequent reaction.

A part of the resultant coarse product of 6,6-dimethoxy-2-methylheptanoic acid methyl ester was purified by column chromatography, to obtain 6,6-dimethoxy-2-methylheptanoic acid methyl ester in the form of colorless oil.

¹H-NMR (CDCl₃, 300 MHz): d1.15 (3H, d, J=7.0 Hz), 1.24 (2H, s), 1.27-1.47 (3H, m), 1.56-1.74 (3H, m), 2.45 (1H, dt, J=7.0, 14.0 Hz), 3.15 (6H, s), 3.67 (3H, s).

Reference Example 5

Synthesis of 7-hydroxy-6-methylheptan-2-one (No. 1)

1.90 g (content 84.4%, 7.3 mmol) of a racemate of 6,6-dimethoxy-2-methylheptanoic acid methyl ester was dissolved in 4.8 g of THF, and 0.93 g (21.9 mmol) of lithium chloride and 1.66 g (content 90%, 39.5 mmol) of sodium borohydride were added sequentially and mixed. Next, 8.80 g of methanol was dropped at room temperature into the reaction mixture over a period of 4 hours, then, the mixture was stirred at the same temperature overnight. Next, 32.07 g of 5% hydrochloric acid was dropped into the reaction mixture at room temperature, to obtain 45.3 g of a uniform solution containing 0.96 g (yield 90.7%) of 7-hydroxy-6-methylheptan-2-one.

Reference Example 6

Synthesis of 7-hydroxy-6-methylheptan-2-one (No. 2)

0.74 g (content 80%, 15.6 mmol) of lithium aluminum hydride was suspended in 7.0 g of THF, and the resultant suspension was cooled to 0° C. Next, 2.37 g(content 84.4%, 9.2 mmol) of 6,6-dimethoxy-2-methylheptanoic acid methyl ester was dissolved in 3.0 g of THF to give a solution which was then dropped into the above-described suspension at 0° C. over a period of 1.5 hours. Next, the reaction mixture as stirred at the same temperature for 3 hours, then, 1.47 g (45.9 mmol) of methanol was dropped to quench unreacted lithium aluminum hydride. Then, 2.74 g of a 2% sodium hydroxide aqueous solution was dropped at room temperature into the reaction mixture, then, the generated aluminum hydroxide was removed by filtration using Radiolite (filtration aid, trade name: manufactured by Showa Chemical Industry Co., Ltd.), subsequently, an acid treatment was performed, to obtain a uniform solution containing 1.07 g (yield 80.9%) of 7-hydroxy-6-methylheptan-2-one.

Example 6

Synthesis of (S)-6,6-dimethoxy-2-methylheptanoic acid methyl ester 21.52 g (content 94.0%, 0.117 mol) of (S)-2-methyl-6-oxoheptanoic acid methyl ester was dissolved in 37.2 g (1.16 mol) of methanol, then, 62.4 g (0.59 mol) of methyl orthoformate and 0.22 g (1.2 mmol) of p-toluenesulfonic acid monohydrate were added and mixed. Then, the reaction mixture was heated up to 65° C., and reacted at the same temperature for 3 hours. After completion of the reaction, the reaction mixture was cooled down to room temperature. Next, to the reaction mixture was added 61 g of toluene and 40.4 g of a 3% sodium hydrogen carbonate aqueous solution and the mixture was sufficiently stirred. After liquid-partitioning, the resultant organic layer was concentrated under reduced pressure, to obtain 25.14 g (content 96.2%, reaction yield 94.4%) of a coarse product of (S)-6,6-dimethoxy-2-methylheptanoic acid methyl ester. The above-described coarse product of (S)-6,6-dimethoxy-2-methylheptanoic acid methyl ester was used as it is in the subsequent reaction. A part of the resultant coarse product of (S)-6,6-dimethoxy-2-methylheptanoic acid methyl ester was purified by column chromatography to obtain (S)-6,6-dimethoxy-2-methylheptanoic acid methyl ester in the form of colorless oil.

$[\alpha]_D^{27} = 22.6°$ (5.01% in EtOH)

Example 7

Synthesis of (S)-7-hydroxy-6-methylheptan-2-one

A solution prepared by dissolving 5.13 g (content 96.2%, 22.6 mmol) of (S)-6,6-dimethoxy-2-methylheptanoic acid methyl ester in 10 g of THF was dropped at room temperature into a suspension prepared by adding 15 g of THF to 0.65 g (content 90%, 26.6 mmol) of lithium borohydride. Next, the reaction mixture was heated up to 55° C., and reacted at the same temperature for 9 hours, to give (S)-6,6-dimethoxy-2-methylheptanol. Next, into this reaction mixture, 7.32 g of methanol was dropped at room temperature over a period of about 1 hour, then, the mixture was stirred at the same temperature for 4 hours. Next, into this reaction mixture, 25.08 g of 5% hydrochloric acid was dropped at room temperature, and the mixture was further stirred at the same temperature for 30 minutes. This solution was extracted twice with 15 g and 12.5 g of methyl isobutyl ketone, then, the resultant organic layers were combined, and washed twice with 10 g of 15% sodium carbonate aqueous solution, to obtain 51.7 g of a MIBK solution containing 2.95 g (yield 89.5%) of (S)-7-hydroxy-6-methylheptan-2-one. The solvent was distilled off under reduced pressure to obtain 3.68 g of a coarse product of (S)-7-hydroxy-6-methylheptan-2-one as a pale yellow oil. This may be used in the subsequent reaction without purification, or if necessary, may be purified by distillation under reduced pressure. A part of the resultant coarse product of (S)-7-hydroxy-6-methylheptan-2-one was purified by distillation, to obtain (S)-7-hydroxy-6-methylheptan-2-one in the form of colorless oil.

$[\alpha]_D^{27} = -13.9°$ (5.03% in EtOH)

Reference Example 7

Acquisition of Esterase

To 10 ml of sterilized liquid medium (prepared by dissolving 5 g of glycerol, 6 g of yeast extract, 4 g of mono-potassium phosphate and 9.3 g of di-potassium phosphate in 1000 ml of water) was added 10 μl of a 50 mg/ml ampicillin aqueous solution and 0.1 ml of a glycerol stock of *E. coli* JM105/pYHNK2 strain (see, JP-A No. 2001-46084), and the mixture was shaken at 30° C. for 9 hours (the resultant culture liquid is described as culture liquid A).

To 15000 ml of sterilized liquid medium (prepared by dissolving 225 g of glycerol, 150 g of yeast extract, 225 g of general amino acid F, 60 g of mono-potassium phosphate, 36 g of magnesium sulfate, 0.6 g of ferrous sulfate heptahydrate and calcium chloride dihydrate in 13000 ml of water, and further adding water to give a total amount of 15000 ml) was added a 4 M phosphoric acid aqueous solution and 14% (W/W) ammonia water to attain pH 7.0. To this was added 7.5 ml of the above-described culture liquid A, and cultured while stirring under ventilation at 30° C. 14 hours after initiation of culture, sterilized liquid medium (prepared by dissolving 280 g of yeast extract and 420 g of general amino acid F in a mixture of 1100 g of water and 1500 g of glycerol) was added gradually. 18 hours after initiation of culture, isopropyl thio-β-D-galactoside was added to attain 50 μM.

40 hours after initiation of culture, 1950 ml of ethanol was added to the culture liquid, and the mixture was further stirred for 24 hours at 30° C. Thereafter, 6000 g of this mixture was mixed with 6200 g of water. This solution was subjected to continuous centrifugal treatment (20000 rpm, flow rate 130 g/min), to obtain 11200 g of centrifuged supernatant. To this centrifuged supernatant was added 220 g of Radiolite #200 (trade name of Showa Chemical Industry Co., Ltd.) and the mixture was stirred, and further, filtrated through Radiolite #200 to obtain a protein clear solution.

Reference Example 8

Immobilization Esterase

Water-washed DIAION HP20SS (trade name of Mitsubishi Chemical Corporation) (prepared by mixing 12 g of DIAION HP20SS and 300 ml of water and stirring the mixture for 30 minutes, filtrating the mixture, and further, washing with 400 ml of water) and 600 g of the protein clear solution produced in Reference Example 7 were mixed, and stirred at 10° C. for 18 hours. Thereafter, the mixture was filtrated and washed with 400 g of water, to obtain 12.5 g of an immobilized enzyme.

INDUSTRIAL APPLICABILITY

According to the production method of the present invention, optically active (S)-7-hydroxy-6-methylheptan-2-one (I) and its precursor optically active (S)-2-methyl-6-oxoheptanoate (III) can be industrially produced simply and efficiently. This optically active (S)-7-hydroxy-6-methylheptan-2-one (I) is useful as a $C_7$ to $C_{12}$ building block in synthesis of Epothilone derivatives to be used as an anti-cancer agent.

The invention claimed is:

1. A method of producing an optically active (S)-2-methyl-6-oxoheptanoate, comprising allowing a R-body preferentially hydrolyzable *Aspergillus* microorganism-derived esterase to act on a 2-methyl-6-oxoheptanoate of the formula (II):

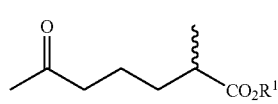

(II)

(wherein, $R^1$ represents an alkyl group having 1 to 5 carbon atoms)

to cause optical resolution, thereby producing an optically active (S)-2-methyl-6-oxoheptanoate of the formula (III):

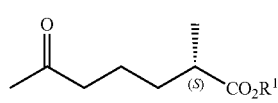

(III)

(wherein, $R^1$ represents the same meaning as described above).

2. The production method according to claim 1, further comprising a step of protecting a carbonyl group of the optically active (S)-2-methyl-6-oxoheptanoate of the formula (III):

(III)

(wherein, $R^1$ represents an alkyl group having 1 to 5 carbon atoms)

to obtain an optically active (S)-ketal ester of the formula (IV):

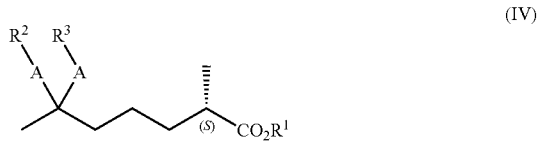

(IV)

(wherein, A represents an oxygen atom or sulfur atom, $R^1$ represents the same meaning as described above, and $R^2$ and $R^3$ represent each independently an alkyl group having 1 to 5 carbon atoms, or are mutually connected to represent an alkylene group having 2 to 5 carbon atoms).

3. The production method according to claim 2, further comprising a step of reducing the optically active (S)-ketal ester of the formula (IV):

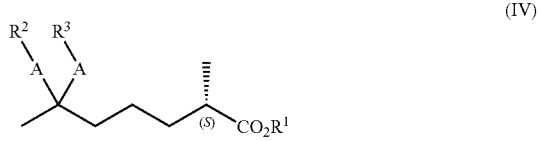

(IV)

(wherein, A, $R^1$, $R^2$, and $R^3$ represent the same meanings as described above)

to obtain an optically active (S)-ketal alcohol of the formula (V):

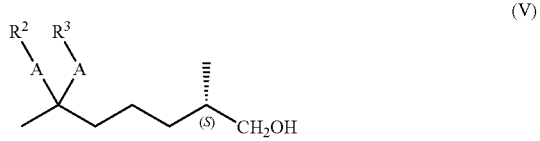

(V)

(wherein, A, $R^2$ and $R^3$ represent the same meanings as described above).

4. A method of producing optically active (S)-7-hydroxy-6-methylheptan-2-one of the formula (I), comprising the steps of allowing a R-body preferentially hydrolyzable *Aspergillus* microorganism-derived esterase to act on a 2-methyl-6-oxoheptanoate of the formula (II):

(II)

(wherein, R¹ represents the same meaning as described above)

to cause optical resolution, thereby producing an optically active (S)-2-methyl-6-oxoheptanoate of the formula (III):

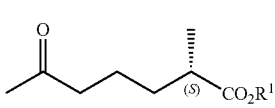
(III)

(wherein, R¹ represents the same meaning as described above), protecting a carbonyl group of the optically active (S)-2-methyl-6-oxoheptanoate of the formula (III) to obtain an optically active (S)-ketal ester of the formula (IV):

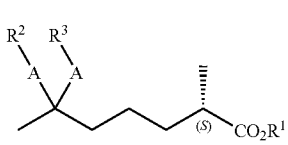
(IV)

(wherein, A, R¹, R² and R³ represent the same meanings as described above), reducing the optically active (S)-ketal ester of the formula (IV) to obtain an optically active (S)-ketal alcohol of the formula (V):

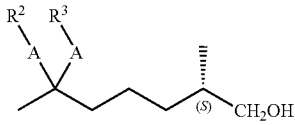
(V)

(wherein, A, R² and R³ represent the same meanings as described above), and de-protecting the optically active (S)-ketal alcohol of the formula (V) to obtain optically active (S)-7-hydroxy-6-methylheptan-2-one of the formula (I):

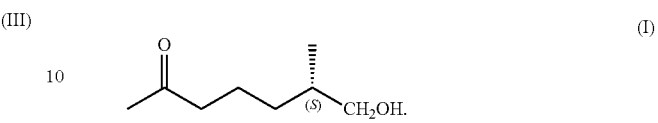
(I)

5. The production method according to claim 1, wherein the optically active (S)-2-methyl-6-oxoheptanoate of the formula (III) has an optical purity of 95 to 100% ee.

6. The production method according to claim 1, wherein R¹ is a methyl group.

7. The production method according to claim 2, wherein R² and R³ are each a methyl group or are mutually connected to represent an ethylene group or propylene group.

8. The production method according to claim 1, wherein the *Aspergillus* microorganism is *Aspergillus flavus*.

9. The production method according to claim 1, wherein the *Aspergillus* microorganism is *Aspergillus flavus* ATCC11492 strain.

10. The production method according to claim 4, wherein the optically active (S)-2-methyl-6-oxoheptanoate of the formula (III) has an optical purity of 95 to 100% ee.

11. The production method according to claim 4, wherein R¹ is a methyl group.

12. The production method according to claim 4, wherein the *Aspergillus* microorganism is *Aspergillus flavus*.

13. The production method according to claim 4, wherein the *Aspergillus* microorganism is *Aspergillus flavus* ATCC11492 strain.

* * * * *